United States Patent [19]

Wang et al.

[11] Patent Number: 4,593,089

[45] Date of Patent: Jun. 3, 1986

[54] FLUORESCENT POLARIZATION IMMUNOASSAY UTILIZING SUBSTITUTED TRIAZINYLAMINOFLUORESCEIN AMINOGLYCOSIDES

[75] Inventors: Chao-Huei J. Wang, Gurnee; Stephen D. Stroupe, Libertyville; Michael E. Jolley, Round Lake, all of Ill.

[73] Assignee: Abbott Laboratories, North Chicago, Ill.

[21] Appl. No.: 546,778

[22] Filed: Oct. 31, 1983

Related U.S. Application Data

[60] Division of Ser. No. 325,872, Nov. 30, 1981, Pat. No. 4,420,568, which is a continuation-in-part of Ser. No. 173,553, Jul. 30, 1980, abandoned.

[51] Int. Cl.[4] .................. C07H 15/232; C07H 15/234
[52] U.S. Cl. .................................... 536/13.6; 536/13.7; 536/14; 536/16.8; 536/17.4; 436/536
[58] Field of Search .................. 536/13.6, 13.7, 14, 536/16.8, 17.4

[56] References Cited

U.S. PATENT DOCUMENTS 4,226,978 10/1980 Boguslaski et al. ............... 536/13.7
4,420,568 12/1983 Wang et al. ........................ 435/536

OTHER PUBLICATIONS

Sheldrick et al. "Reprint from Nature", vol. 271, No. 5642, pp. 223-225, Jan. 19, 1978.
Blakeslee et al., "Jour. of Immunological Methods", 13 (1976) pp. 305-320.
Watson et al., "Clinica Chimica Acta." vol. 73 (1976) pp. 51-5.
Spencer et al., "Clinical Chemistry", vol. 19, No. 8, 1973, pp. 838-844.
Blakeslee, "Jour. of Immunological Methods", 17 (1977) pp. 361-364.
McGregor et al., "Clinica Chimica Acta.", 83 (1978) pp. 161-166.
Kobayashi et al., "Clinica Chimica Acta", 92 (1979) pp. 241-247.

Primary Examiner—Johnnie R. Brown
Attorney, Agent, or Firm—James L. Wilcox

[57] ABSTRACT

This disclosure relates to a method and reagents for determining ligands in biological fluids such as serum, plasma, spinal fluid, amnionic fluid and urine. In particular, this disclosure relates to a fluorescent polarization immunoassay procedure and to a novel class of tracer compounds employed as reagents in such procedures. The procedure disclosed combines the specificity of an immunoassay with the speed and convenience of fluorescent polarization techniques to provide a means for determining the amount of a specific ligand present in a sample.

7 Claims, No Drawings

FLUORESCENT POLARIZATION IMMUNOASSAY UTILIZING SUBSTITUTED TRIAZINYLAMINOFLUORESCEIN AMINOGLYCOSIDES

This is a division of application Ser. No. 325,872, filed Nov. 30, 1981, now U.S. Pat. No. 4,420,568, which is a continuation-in-part of application Ser. No. 173,553, filed July 30, 1980, now abandoned.

BACKGROUND OF THE INVENTION

The present invention relates to a method and reagents for determining ligands in biological fluids such as serum, plasma, spinal fluid, amnionic fluid and urine. In particular, the present invention relates to a fluorescent polarization immunoassay procedure and to tracers employed as reagents in such procedures. The fluorescent polarization immunoassay procedure of the present invention combines the specificity of an immunoassay with the speed and convenience of fluorescent polarization techniques to provide a means for determining the amount of a specific ligand present in a sample.

Competitive binding immunoassays for measuring ligands are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitively measured and is inversely proportional to the quantity of ligand in the test sample.

In general, fluorescent polarization techniques are based on the principle that a fluorescent labeled compound when excited by linearly polarized light will emit fluorescence having a degree of polarization inversely related to its rate of rotation. Therefore, when a molecule such as a tracer-antibody conjugate having a fluorescent label is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescence polarization provides a quantitive means for measuring the amount of tracer-antibody conjugate produced in a competitive binding immunoassay.

Various fluorescent labeled compounds are known in the art. U.S. Pat. No. 3,998,943 describes the preparation of a fluorescently labeled insulin derivative using fluorescein isothiocyanate (FITC) as the fluorescent label and a fluorescently labeled morphine derivative using 4-aminofluorescein hydrochloride as the fluorescent label. Blakeslee, et al, in *The Journal of Immunological Methods*, 13, 305–320 (1976) described the 5-[(4,6-dichlorotriazin-2-yl)-amino]fluorescein derivaties of immunoglobulins (IgG) having molecular weights of at least 160,000. Blakeslee fails to teach or suggest the use of the various fluorescein derivatives in conjunction with fluorescent polarization immunoassay techniques.

SUMMARY OF THE INVENTION

The present invention encompasses a method for determining ligands in a sample comprising intermixing with said sample a biologically acceptable salt of a tracer of the formula:

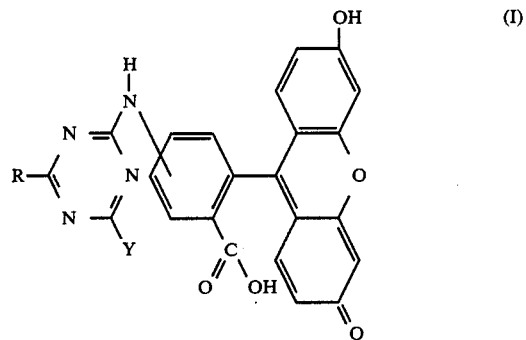

wherein
Y is halo or lower alkyl; and
R is a ligand-analog wherein said ligand-analog has at least one common epitope with said ligand so as to be specifically reconizable by a common antibody;
and an antibody capable of specifically recognizing said ligand and said tracer; and then determining the amount of tracer-antibody conjugate by fluorescence polarization techniques as a measure of the concentration of said ligand in the sample.

The invention further relates to a novel class of tracers of formula (I) and biologically acceptable salts thereof, which are useful in reagents in the above-described method. The methods and tracers of the present invention are particularly useful in quantitatively monitoring therapeutic drug concentrations in serum and plasma.

DETAILED DESCRIPTION OF THE INVENTION

The term "ligand" as used herein refers to a molecule in particular a low molecular weight hapten, to which a receptor, normally an antibody, can be obtained or formed. Haptens are protein-free bodies, generally of low molecular weight that do not induce antibody formation when injected into an animal, but are reactive to antibodies. Antibodies to hapten are generally raised by first conjugating the haptens to a protein and injecting the conjugate product into an animal. The resulting antibodies are isolated by conventional antibody isolation techniques.

The ligands determinable by the method of the present invention vary over a wide molecular weight range. Although high molecular weight ligands may be determined, for best results, it is generally preferable to employ the methods of the present invention to determine ligands of low molecular weight, generally in a range of 50 to 4000. It is more preferred to determine ligands having a molecular weight in a range of 100 to 2000.

The novel tracer of the present invention includes compounds of formula (I) wherein the ligand-analogs represented by R include radicals having a molecular weight within a range of 50 to 4000. The preferred novel tracers include compounds of formula (I) wherein the ligand-analogs represented by R include radicals having a molecular weight within a range of 100 to 2000.

Representative of ligands determinable by the methods of the present invention include steroids such as estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine, histamine, serotonin, prostaglandins such as PGE, PGF, PGA; antiasthamatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortrptyline, amitriptyline, imipramine and desipramine; and the like as well as the metabolites thereof.

Additional ligands that may be determined by the methods of the present invention include drugs of abuse such as morphine, heroin, hydromophone, oxymorphone, metapon, codeine, hydrocodone, dihydrocodiene, dihydrohydroxy codeinone, pholcodine, dextromethorphan, phenazocine and deonin and their metabolities.

The tracers of the present invention generally exist in an equilibrium between their acid and ionized states, and in the ionized state are effective in the method of the present invention. Therefore, the present invention comprises the tracers in either the acid or ionized state and for convenience, the tracers of the present invention are structurally represented herein in their acid form. When the tracers of the present invention are present in their ionized state, the tracers exist in the form of biologically acceptable salts. As used herein, the term "biologically acceptable salts" refers to salts such as sodium, potassium, ammonium and the like which will enable the tracers of the present invention to exist in their ionized state when employed in the method of the present invention. Generally, the tracers of the present invention exist in solution as salts, the specific salt results from the buffer employed, i.e., in the presence of a sodium phosphate buffer, the tracers of the present invention will generally exist in their ionized state as a sodium salt.

The tracers of the present invention comprise a ligand-analog represented by R linked to a triazinylaminofluorescein moiety of the formula:

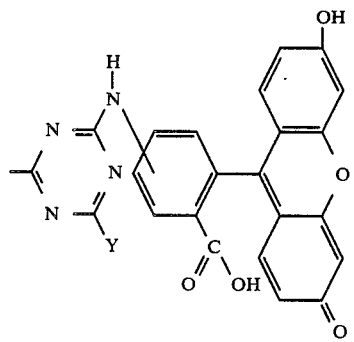
(II)

wherein Y is above defined. Representation of the "lower alkyl" groups represented by Y include alkyl radicals having from 1 to 4 carbon atoms, such as, for example, methyl, ethyl, propyl, isopropyl, n-butyl, sec-butyl, t-butyl, and the like. Illustrative of the "halo" groups represented by Y include fluoro, chloro, iodo and bromo. It is preferred that Y is chloro or bromo and most preferred that Y is chloro.

The term ligand-analog as used herein refers to a mono- or polyvalent radical a substantial proportion of which has the same spatial and polar organization as the ligand to define one or more determinant or epitopic sites capable of competing with the ligand for the binding sites of a receptor. A characteristic of such ligand-analog is that is possesses sufficient structural similarity to the ligand of interest so as to be recognized by the anitbody for the ligand. For the most part, the ligand analog will have the same or substantially the same structure and charge distribution (spatial and polar organization) as the ligand of interest for a significant portion of the molecular surface. Since frequently, the linking site for a hapten will be same in preparing the antigen for production of antibodies as used for linking to the ligand, the same portion of the ligand analog which provides the template for the antibody will be exposed by the ligand analog in the tracer.

In general, the class of ligand analogs represented by R are derived from the corresponding ligand by removal of a reactive hydrogen atom, i.e., a hydrogen atom bonded to a hydroxy oxygen or a reactive amine (primary or secondary) or by the formation of an amino derivative of the ligand wherein an imino group

replaces one or more atoms originally present in the ligand, at the site of binding to the triazinylaminofluorescein moiety. Illustrative of ligands which upon the removal of a reactive hydrogen may form a ligand-analogs represented by R include for example, procainamide, thyroxine, quinidine and the aminoglycoside antibiotics. Illustrative of ligands whose amino derivatives are useful as ligand-analog include theophylline, valproic acid, phentobarbital, phenytoin, primidone, disopyramide, digoxin, chloramphenicol, salicylate, acetaminophen, carbamazepine, desimpramine and nortriptyline. In addition, a ligand may be structurally modified by the addition or deletion of one or more functional groups to form a ligand-analog, while retaining the necessary epitope sites for binding to an antibody. However, it is preferred that such modified ligand-analogs be bonded to the triazinylaminofluorescein moiety through an imino or oxy group.

The tracers of the present invention are generally prepared in accordance with the following procedure:

R—X (III)

wherein R is above-defined and X is a reactive hydrogen; is reacted with a compound of the formula:

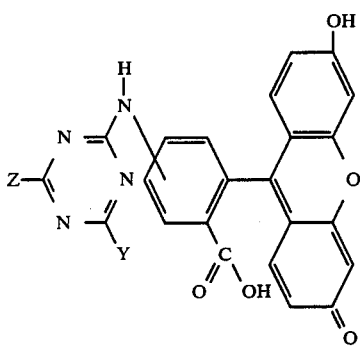

wherein Z is halo and Y is above-defined, and wherein the amino group is bonded to the 4 or 5 position of the benzoic acid ring; under basic conditions in the presence of an intert solvent to yield a compound of formula (I).

It should be noted that if a compound of formula (III) has more than one reactive hydrogen, a mixture of products of formula (I) may result upon reaction with a triazinylaminofluorescein moiety. For example, when the ligand of interest is an antibiotic such as, for example, an aminoglycoside, the corresponding ligand-analog is generally derived from a ligand having multiple reactive amine hydrogens. Replacing any of such reactive amine hydrogens with a triazinylaminofluorescein moiety will produce a tracer of formula (I). Therefore, the reaction product resulting from the reaction of an antibiotic such as an aminoglycoside, with triazinylaminofluorescein will generally be a mixture of products represented by formula (I). All of these reaction products, individually or in combination are effective as tracers in a fluorescent polarization immunoassay technique.

The temperature at which the reaction for preparing the tracers of this invention proceeds is not critical. The temperature should be one which is sufficient so as to initiate and maintain the reaction. Generally, for convenience and economy, room temperature is sufficient. In preparing the tracers of the present invention, the ratio of reactants is not narrowly cirtical. For each mole of a compound of formula (II), one should employ one more of a compound of formula (III) to obtain a reasonably yield. It is preferred to employ an excess of compound of formula (III) for ease of reaction and recovery of the reaction products.

The compounds of formula (IV) employed as starting materials in the production of the tracers of this invention are prepared in accordance with the method described by Blakeslee, et al. (supra). It should be noted that two isomers of compound (IV) generally exist. Isomer I is prepared from 5-aminofluorescein and Isomer II is prepared from 4-amino-fluorescein. It is preferred to employ Isomer I or Isomer II and mixtures thereof as starting materials in the preparation of the compounds of the present invention.

For ease of handling and recovery of product, the process for preparing the tracers of the present invention is conducted in the presence of an inert solvent. Suitable inert solvents include those solvents which do not react with the starting materials and are sufficient to dissolve the starting materials, and include for example water, methanol, dimethylformamide, dimethylsulfoxide and the like. In order to provide maximum product yields, the reaction preferably proceeds under neutral or basic conditions. If the compound of formula (III) is a reactive amine salt, a suitable base is added to the reaction mixture to form the free base of the reactive amine. Suitable bases include for example triethylamine. The reaction products of formula (I) are generally purified using either thin-layer or column chromatography prior to application in the methods of the present invention.

In accordance with the method of the present invention, a sample containing the ligand to be determined is intermixed with a biologically acceptable salt of a tracer of formula (I) and an antibody specific for the ligand and tracer. The ligand present in the sample and the tracer compete for limiting antibody sites resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, upon exciting the mixture with fluorescent light and measuring the polarization of the fluorescence emitted by a tracer and a tracer-antibody complex, one is able to quantitatively determine the amount of ligand in the sample.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of a ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertical component of the emitted light, the polarization of fluorescence in the reaction mix may be accurately determined. The precise relationship between polarization and concentration of the ligand to be determined is established by measuring the polarization values of calibrators with known concentrations. The concentration of the ligand can be extrapolated from a standard curve prepared in this manner.

The pH at which the method of the present invention is practiced must be sufficient to allow the tracers of formula (I) to exist in their ionized state. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practical at moderate temperatures and preferably at a constant temperature. The temperature will normally range from about 0° to 50° C., more usually from about 15° to 40° C.

The concentration of ligand which may be assayed will generally vary from about $10^{-2}$ to $10^{-13}$M, more usually from about $10^{-4}$ to $10^{-10}$M. Higher concentrations of ligand may be assayed upon dilution of the original sample.

In addition to the concentration range of ligand of interest, considerations such as whether the assay is qualitative, semiquantitative or quantitative, the equipment employed, and the characteristics of the tracer and antibody will normally determine the concentration of the tracer and antibody to be employed. While the concentration of ligand in the sample will determine the range of concentration of the other reagents, i.e., tracer and antibody, normally to optimize the sensitivity of the assay, individual reagent concentrations will be determined empirically. Concentrations of the tracer and antibody are readily ascertained by one of ordinary skill in the art.

As previously mentioned the preferred tracers of the present invention are prepared from 5-[(4,6-dichloro-triazin-2-yl)-amino]fluorescein or 4-[(4,6-dichlorotriazin-2-yl)-amino]fluorescein and exist preferably as isomers of the formula:

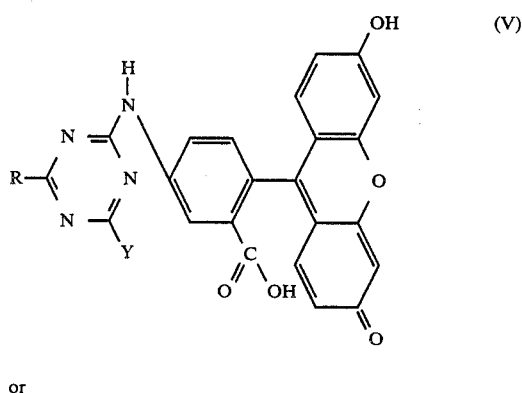

or

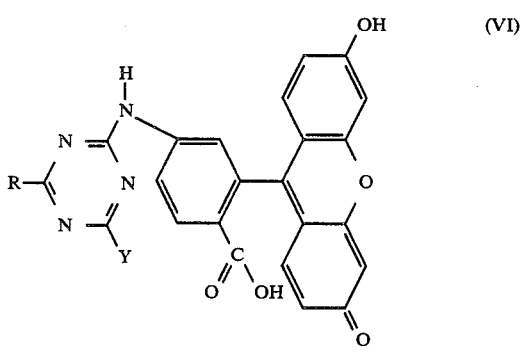

The following illustrative, nonlimiting examples will serve to further demonstrate to those skilled in the art the manner in which specific tracers within the scope of this invention may be prepared. The symbol [DTAF] appearing in the structural formulas illustrating the compounds prepared in the following examples, represents a moiety of the formula:

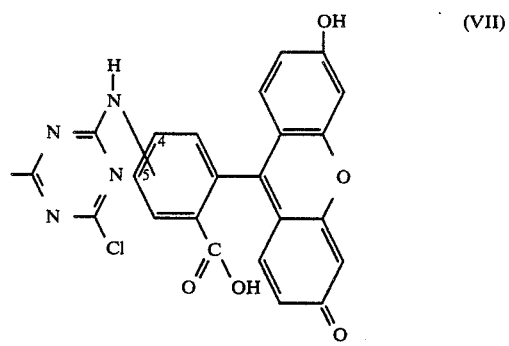

wherein the imino nitrogen is attached to the 4 to 5 position in the above formula depending on the specific triazinylfluorescein isomer employed as the starting material.

EXAMPLE I

Gentamicin sulfate (200 mg) was dissolved in 1 ml of distilled water and the resulting solution was adjusted to pH 9.0 using approximately 0.8 ml of 1.0M sodium hydroxide. 5-[(4,6-dichlorotriazin-2-yl)-amino]fluorescein (20 mg) was dissolved in 1.5 ml of methanol and the resulting methanol solution was added dropwise to the gentamicin solution with stirring. The reaction mixture was allowed to react for one hour. The resultant mixture was chormatographed on a DEAE cellulose medium mesh column using 0.1M phosphate buffer at pH 8.0 as the eluent to yield a gentamicin-DTAf conjugate.

EXAMPLE II

Tobramycin (250 mg) was dissolved in 2 ml of 0.1M carbonate buffer (pH 9.0). 5-[(4,6-dichlorotriazin-2-yl)-amino]fluorescein (20 mg) was dissolved in 1 ml of methanol and the resulting methanol solution was added to 1 ml of the tobramycin solution. After approximately five minutes, the rection mixture was purified by chormatography on a DEAE cellulose column using 0.1M phosphate buffer at pH 8.0 as the eluent to yield a tobramycin-DTAF conjugate.

EXAMPLE III

Amikacin (9.24 mg) was dissolved in 0.2 ml of water. A suspension containing 4.5 mg of dichlorotriazinyl-aminofluorescein in 0.2 ml of methanol was added to the amikacin solution with stirring. The small particles of 5-[(4,6-dichlorotriazin-2-yl)-amino]fluorescein rapidly dissolved, the reaction mixture was chromatographed on a 17 ml column of DEAE cellulose using pH 8.1 phosphate buffer, 0.1M as the eluent to yield an amikacin-DTAF conjugate.

EXAMPLE IV

Streptomycin sulfate (200 mg) was dissolved in 15 ml of water and the resulting solution was adjusted to pH 10.5 using 1N sodium hydroxide. To the streptomycin solution was dropwise added with stirring, 20 mg of 5-[(4,6-dichlorotriazin-2-yl)-amino]fluorescein dissolved in 1.5 ml of dimethylsulfoxide. 4 ml of the reaction mixture was chromatographed on a DEAE cellulose column using a 0.1M phosphate buffer (pH 8.0) as the eluent to yield a streptomycin-DTAF conjugate.

EXAMPLE V

Neomycin sulfate (200 mg) was dissolved in 3 ml of water and the resulting solution was adjusted to pH 9.0 using 6N sodium hydroxide. To the neomycin solution was dropwise added with stirring 20 mg of 5-[(4,6-dichlorotriazin-2-yl)-amino]-fluorescein dissolved in 1.5 ml of dimethylsulfoxide. 2 ml of the reaction mixture was chromatographed on a DEAE cellulose column using 0.1M phosphate buffer (pH 8.0) as the eluent to yield a neomycin-DTAF conjugate.

EXAMPLE VI

Vancomycin hydrochloride (100 mg) was dissolved in 100 ml of water and the resulting solution was adjusted to pH 9.1 using 1N sodium hydroxide. The vancomycin solution was then adjusted to pH 7 using 1N HCl after which time 20 mg of 5-[(4,6-dichlorotriazin-2-yl)-amino]fluorescein in 2 ml of dimethylsulfoxide was added with stirring. A crude product formed which was purified using silica gel thin-layer chromatography techniques employing a developing solvent comprising a chloroform-methanol-water (4:4:1) mixture to yield a vancomycin-DTAF conjugate.

EXAMPLE VII

To 1.79 g of para-acetamidobenzoic acid and 1.15 g of N-hydroxysuccinimide dissolved in 15 ml of pyridine was added 2.3 g of N,N'-dicyclohexylcarbodiimide. The reaction mixture was cooled at 4° C. for two hours and then filtered to remove crystals which had formed. The crystals were washed with approximately 2 ml acetone and the pyridine filtrate and acetone washings were then combined. To the combined mixture was added 0.88 g of N-ethylethylenediamine. The resulting mixture was stirred for two hours and then cooled at 4° C. for about twenty-four hours to yield a second crop of crystals. The crystals were removed from the mixture by filtration and then rinsed with acetone. The two crops of crystals (approximately 2.0 g) were combined and then dissolved in 50 ml of distilled water. The pH of the resulting mixture was adjusted to pH 10 using a 6N sodium hydroxide solution. A white precipitate, desethyl-N-acetylprocainamide formed and was removed by filtration and dried in a dessicator. To 10 mg of the desethyl-N-acetyl-procainamide was added 10 mg of 4-[(4,6-dichlorotriazin-2-yl)-amino]fluorescein dissolved in 1 ml of methanol. The mixture was allowed to react for ten minutes, and the crude product which had formed was purified using silica gel thin-layer chromatographic techniques employing a developing solvent comprising a 1:1 mixture of chloroform:acetone to yield a desethyl-N-acetyl-procainamide-DTAF conjugate of the formula:

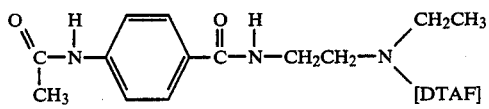

EXAMPLE VIII

The procedure of Example IV was employed using 0.9 g of ethylenediamine in lieu of N-ethylethylenediamine. The reaction mixture was stirred for one hour, and cooled for 1.5 hours. Methanol was used in lieu of a 1:1 mixture of chloroform:acetone as the developing solvent in the purification of the crude product to yield an N-p-acetamidobenzoyl ethylene diamine-DTAF conjugate of the formula:

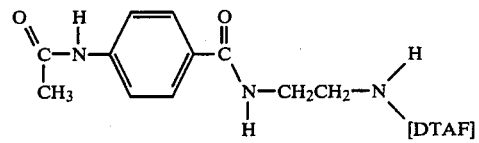

EXAMPLE IX

A mixture containing desethyl-N-acetyl procainamide (1.25 g) (prepared as in Example VII and 0.8 g of chloroacetyl chloride dissolved in 25 ml of acetone was refluxed for two hours. The reaction mixture was filtered and the filtrate evaporated to yield a yellow residue. The yellow residue and 0.75 g of sodium iodide were dissolved in 20 ml of acetone and refluxed for one hour. The resulting mixture was filtered and the filtrate evaporated to dryness to yield a red residue which was then dissolved in 20 ml of methanol. To the methanol solution was added 20 ml of concentrated ammonium hydroxide and the resulting mixture was refluxed for 1.5 hours. The mixture was cooled and then extracted twice with 20 ml of chloroform. The combined extracts were dried over sodium sulfate, filtered and evaporated to yield N-p-acetamidobenzoyl-N'-ethyl-N'-aminoacetylethylene diamine. To 10 mg of N-p-acetamidobenzoyl-N'-ethyl-N'-aminoacetylethylene diamine was added 10 mg of 5-[(4,6-dichlorotriazin-2-yl)-amino]fluorescein dissolved in 1 ml of methanol and the reaction was allowed to proceed for ten minutes until a crude product had formed. The crude product was purified using silica gel thin-layer chromatographic techniques employing a developing solvent comprising a 1:1 mixture of chloroform:acetone to yield an N-P-acetamidobenzoyl-N'-ethyl-N'-aminoacetylethylene diamine-DTAF conjugate of the formula:

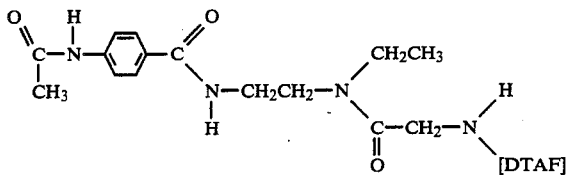

EXAMPLE X

To 1.1 g of primidone dissolved in 10 ml of concentrated sulfuric acid was slowly added a solution containing 1 ml of concentrated nitric acid and 2 ml of concentrated sulfuric acid. The reaction mixture was shaken at room temperature for forty-five minutes. The reaction mixture was then poured over 50 ml ice and crystals of para-nitroprimidone that had formed were filtered and then rinsed with water. The crystals (1.17 g, having a melting point 225°-228° C.) were dissolved in 200 ml of hot ethanol. To the ethanol solution was added 1.5 g of iron powder and 100 ml of water. The resultant mixture was heated to boiling, and then 2 ml of concentrated hydrochloric acid was added. The resultant mixture was refluxed for two hours and the hot mixture was filtered and the filtrate to yield 0.8 g of brown hydroscopic crystals. 5 mg of 5-[(4,6-dichlorotriazin-2-yl)-amino]fluorescein and 5 mg of the brown crystals were dissolved in 0.5 ml of methanol. The reaction was complete in 10 minutes to yield a crude product which was purified by silica gel thin-layer chromatography using 3:1 mixture of chloroform: methanol as the developing solvent. The product was further purified using thin-layer chromatography employing a 2:1 mixture of chloroform:methanol to yield an amino-primidone-DTAF conjugate of the formula:

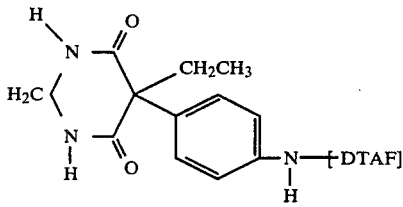

EXAMPLE XI

To delta-valerolactam (10 g) dissolved in 80 ml of dry tetrahydrofuran, under a dry nitrogen atmosphere was deopwise added n-butyllithium (1.6M, 125 ml) in hexane while the reaction mixture was chilled in a dry ice-acetone bath. After all the n-butyllithium was added, the reaction mixture was stirred at room temperature for one hour, refluxed for thirty minutes, and cooled to room temperature. 1-Bromopropane (12.3 g) was slowly added to the reaction mixture while the mixture was chilled in an ice bath. The reaction mixture was then stirred for sixteen hours at room temperature. 100 ml of water was added slowly to the reaction mixture and the resulting mixture was stirred at room temperature for thirty minutes. The layers separated and the aqueous layers were combined, dried over sodium sulfate, and then evaporated to yield 12.4 g (88% yield) of a dark, heavy oil, which crystallized on standing. The crystals were recrystallized from petroleum ether to yield 5.4 g of α-propylvalerolactam (m.p. 75°–76° C.). A portion of the α-propylvalerolactam (2.8 g) was refluxed in 25 ml of 6N hydrochloric acid under a nitrogen atmosphere for six hours. The water was evaporated to yield 2-propyl-5-amino-pentanoic acid (2.0 g; 51% yield) and recrystallized from ethanol-petroleum ether to yield a solid (m.p. 71°–73° C.). Equimolar amounts of 2-propyl-5-amino-pentanoic acid and 5-[(4,6-dichlorotriazin-2-yl)-amino]fluorescein were dissolved in methanol. The reaction was completed in about ten minutes to yield a crude product which was purified by silica gel thin-layer chromatography with chloroform/methanol (3:1) as the developing solvent to yield a 2-propyl-5-amino-pentanoic acid-DTAF conjugate of the formula:

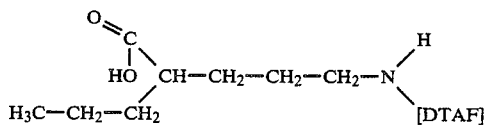

EXAMPLE XII

The procedure of Example VIII was employed utilizing 2-ethyl-5-aminopentanoic acid in lieu of 2-propyl-5-amino-pentanoic acid to yield a 2-ethyl-5-amino-pentanoic acid-DTAF conjugate of the formula:

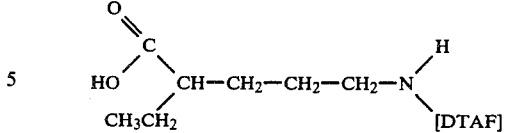

EXAMPLE XIII

To a mixture containing 5 mg of 5-[(4,6-dichlorotriazin-2-yl)-amino]fluorescein dissolved in methanol and 5 mg of D-thyroxine was dropwise added dimethylsulfoxide until a clear solution was formed. Two drops of triethylamine was added to the reaction mixture and the reaction was allowed to proceed for 16 hours. A crude product has formed which was then purified by silica gel thin-layer chromatography using a 3:1 mixture of chloroform:methanol as the developing solvent to yield a 3,3',5,5'-tetraiodo-D-thyronine-DTAF conjugate of the formula:

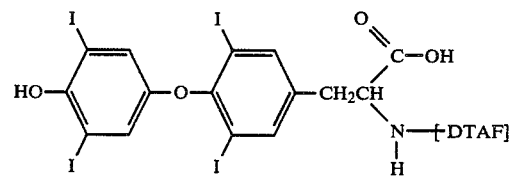

EXAMPLE XIV

The procedure of Example XIII was employed utilizing L-thyroxine in lieu of D-thyroxine to yield 3,3',5,5'-tetraiodo-L-thyronine-DTAF conjugate which is an optical isomer of the conjugate formed in Example XIII.

EXAMPLE XV

The procedure of Example XIII was employed utilizing 3,3',5-triiodo-L-thyronine in lieu of D-thyroxine to yield a 3,3',5-triiodo-L-thyronine-DTAF conjugate of the formula:

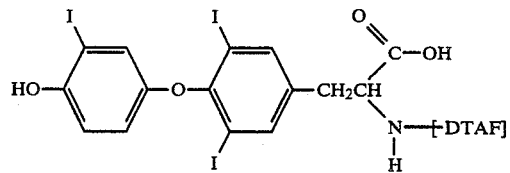

EXAMPLE XVI

A solution containing ammonium acetate (8.0 g), sodium cyanoborohydride (630 mg) and 10,11-dihydro-5H-dibenzo[a,d] cyclohepten-5-one (2.1 g) dissolved in 50 ml of methanol was refluxed for twenty four hours and then evaporated to dryness to yield a tan residue. The residue was dissolved in 25 ml of 2N hydrochloric acid and extracted twice with 25 ml dichloromethane. 6N sodium hydroxide was added to the aqueous phase until the pH of the solution was 14. A brown oil then began to form and the solution was chilled in a freezer for 16 hours. All water in the mixture was evaporated and the residue was taken up in methanol and filtered. The filtrate was evaporated to yield a white residue. 10 mg of 5-[(4,6-dichlorotriazin-2-yl)-amino]fluorescein and 10 mg of the white residue were dissolved in 1 ml of methanol to yield a crude product which was purified by silica gel thin-layer chromatography using a 1:1 mixture of chloroform:acetone as a developing solvent to yield a 5-amino-10,11-dihydro-5H-dibenzo[a,d]-cycloheptene-DTAF conjugate of the formula:

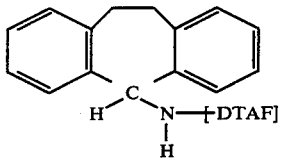

EXAMPLE XVII

A mixture containing 10,11-dihydro-5H-dibenzo[a,d]cyclohepten-5-one (10 g) and dimethylhydrazine (18%) were refluxed for twenty-four hours in 100% ethanol. To the mixture was added 100 ml of distilled water and a yellow solution was extracted with diethyl ether until the extracts were colorless. The combined ether extracts were washed with 25 ml of 2N hydrochloric acid. The organic phase was then dried over sodium sulfate and evaporated to yield dibenzosuberone dimethyl hydrazone as a thick orange oil. This oil (2.0 g) was refluxed for twelve hours in a solution containing 3 g of hydrazine in 10 ml of 100% ethanol. The reaction mixture was poured over 10 ml of ice water then extracted twice with 25 ml of diethyl ether. The combined ether extracts were dried over sodium sulfate and evaporated to dryness to yield dibenzosuberone hydrazone as a yellow oil. 10 mg of 5-[(4,6-dichlorotriazin-2-yl)-amino]fluorescein and 10 mg of dibenzosuberone hydrazone in 1 ml of methanol were allowed to react for 10 minutes to yield a crude product which was purified using silica gel thin-layer chromatography using a 3:1 mixture of chloroform:methanol as a developing solvent to yield a dibenzosuberone hydrazone-DTAF conjugate of the formula:

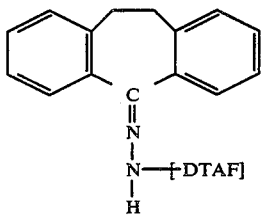

EXAMPLE XVIII 5-(γ-Bromopropylidene)-5H-dibenzo[a,d]-10,11-dihydro cycloheptene and its precursor 5-cyclopropyl-5-hydroxy-5H-dibenzo[a,d]-10,11-dihydrocycloheptene were prepared by the procedure described in *The Journal of Organic Chemistry*, Vol. 27, pages 4134–4137 (1962) by R. D. Hoffsomer, D. Taub, and N. L. Wendler. Procedure (b) for preparation of end product, 5-(γ-aminopropylidene)-5H-dibenzo[a,d]-10,11-dihydrocycloheptene, was employed substituting the bromopropylidene compound for the chloropropylidene compound. 10 mg of 5-[(4,6-dichlorotriazin-2-yl)-amino]fluorescein and 10 mg of the end product were dissolved in 1 ml of methanol. An excess amount of triethylamine was added and the reaction was completed in thirty minutes to yield a crude product which was purified by silica gel thin-layer chromatography using a 2:1 mixture of chloroform:methanol as developing solvent to yield a 5-(γ-aminopropylidene)-5H-dibenzo[a,d]-10,11-dihydrocycloheptene-DTAF conjugate of the formula:

EXAMPLE XIX

To a mixture containing 6.0 g of iminodibenzyl in 30 ml of chloroform was added 6 ml of chloroacetyl chloride and the resultant mixture was refluxed for forty-five minutes. To the reaction mixture was added 60 ml of water and the resultant mixture was stirred for thirty minutes at room temperature. The chloroform layer was separated and dried over sodium sulfate and evaporated to dryness to yield a residue. The residue was dissolved in 25 ml of acetone. A solution containing 4.5 g sodium iodide dissolved in 25 ml of acetone was added to the acetone solution and the resultant mixture was refluxed for thirty minutes. To the reaction mixture was added 100 ml of water and the reaction mixture was extracted twice with 50 ml of chloroform and evaporated to dryness to yield a residue which was then dissolved in 40 ml of methanol. To the methanol solution was added 60 ml of concentrated ammonium hydroxide and the resultant mixture was refluxed for one hour. The reaction mixture was evaporated to dryness and the residue was taken up in 100 ml of chloroform and washed twice with 30 ml of water. The chloroform layer was dried over sodium sulfate and evaporated to dryness to yield 4.5 g of an amine product. A mixture containing 5 mg of 5-[(4,6-dichlorotriazin-2-yl)-amino]-fluorescein and 5 mg of the amine dissolved in 0.5 ml of methanol were allowed to react for 10 minutes to yield a crude product which was purified as in Example XVI to yield a N-aminoacetyliminostibene-DTAF conjugate of the formula:

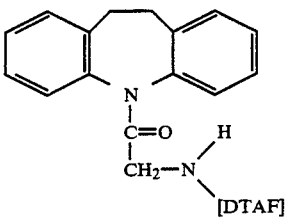

EXAMPLE XX

A mixture containing desipramine hydrochloride (1.33 g) and chloroacetyl chloride (0.8 g) dissolved in 25 ml chloroform was refluxed for two hours. The chloroform was evaporated to yield a residue which was dissolved in 25 ml of acetone. Sodium iodide (0.75 g) was added to the acetone solution and the resultant solution was refluxed for thirty minutes and then filtered. The precipitated salt was rinsed with acetone and the acetone filtrate was evaporated and the residue was taken up in 20 ml of methanol. To the methanol solution was added 20 ml of concentrated ammonium hydroxide and the resultant solution was refluxed for one hour. The reaction mixture was extracted three times with 25 ml of chloroform and combined extracts were dried over sodium sulfate, filtered and evaporated. 5 mg of 5-[(4,6-dichlorotriazin-2-yl)amino]fluorescein and 5 mg of the amine were dissolved in 0.5 ml of methanol. About five drops of dimethylsulfoxide were added to the reaction mixture to dissolve the precipitate. The reaction was completed in ten minutes and yielded a crude product which was purified in accordance with the procedure of Example XVI using a 3:1 mixture of chloroform:methanol as the developing solvent to yield a N-aminoacetyldesipramine-DTAF conjugate of the formula:

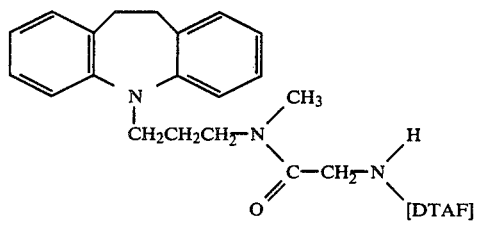

EXAMPLE XXI

5-[(4,6-dichlorotriazin-2-yl)-amino]fluorescein (10 mg) and 8-aminomethyl-theophylline (5 mg) were dissolved in 0.5 ml of dimethylsulfoxide. After five minutes the reaction was complete and yielded a crude product which was purified by silica gel thin-layer chromatography using a 1:1 mixture of chloroform:acetone as the developing solvent to yield an 8-aminomethyl-theophylline-DTAF conjugate of the formula:

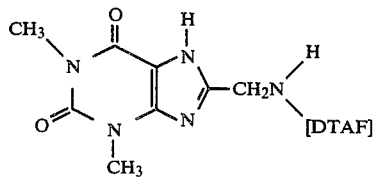

EXAMPLE XXII

The procedure of Example XXI was employed utilizing 8-aminoethyl-theophylline in lieu of 8-aminomethyl-theophylline to yield an 8-aminoethyl-theophylline-DTAF conjugate of the formula:

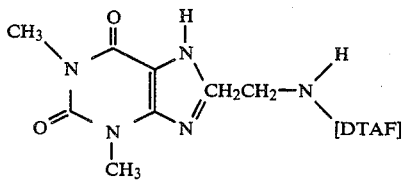

EXAMPLE XXIII

5-[(4,6-dichlorotriazin-2-yl)-amino]fluorescein (5 mg) and anhydrous quinidine (5 mg) were dissolved in 0.5 ml of dimethylformamide. After sixteen hours the reaction was complete and yielded a crude product which was purified by silica gel thin-layer chromatography, using a 3:1 mixture of chloroform:methanol as the developing solvent to yield a quinidine-DTAF conjugate of the formula:

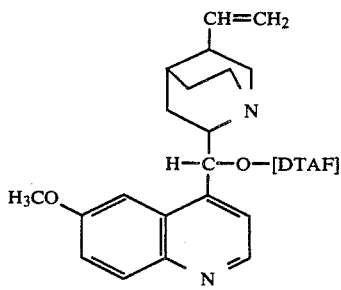

The following tracers were also prepared in accordance with the above procedures:

EXAMPLE XXIV 5-(p-aminobenzamido)-2-propylpentanoic acid-DTAF conjugate

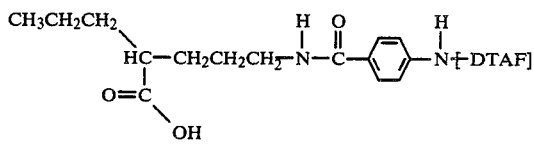

EXAMPLE XXV 1-amino-2-phenyl-2-(2'-pyridyl)-4-diisopropylaminobutane-DTAF conjugate

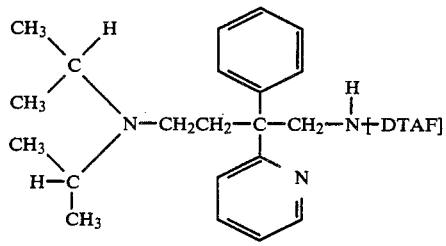

EXAMPLE XXVI 2-phenyl-2-(2'-pyridyl)-4-(diisopropylamino)-butyryl-hydrazine-DTAF conjugate

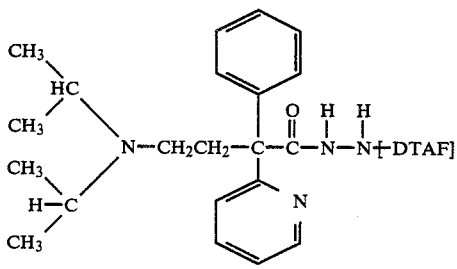

EXAMPLE XXVII 4-aminosalicyclic acid-DTAF conjugate

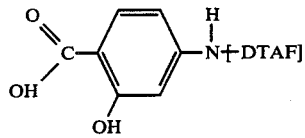

EXAMPLE XXVIII procainamide-DTAF conjugate

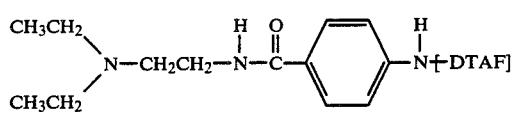

EXAMPLE XXIX 1-hydroxymethyl-2-hydroxy-2-(4'-nitrophenyl)-ethylamine-DTAF conjugate

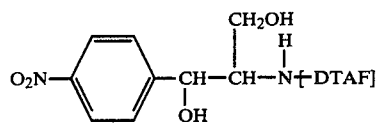

EXAMPLE XXX

2-β-aminoethylphenytoin-DTAF conjugate

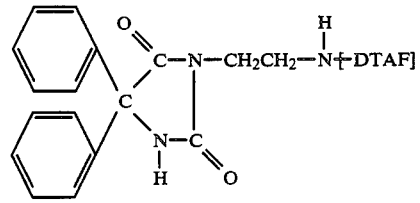

EXAMPLE XXXI 5-aminosalicyclic acid-DTAF conjugate

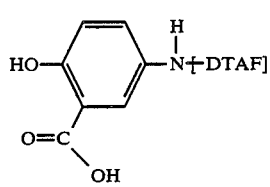

EXAMPLE XXXII propanolol-DTAF conjugate

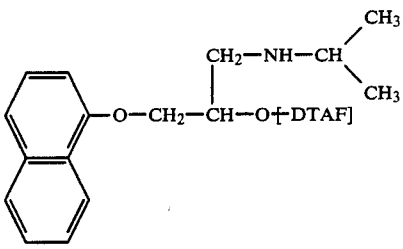

EXAMPLE XXXIII aminophenobarbital-DTAF conjugate

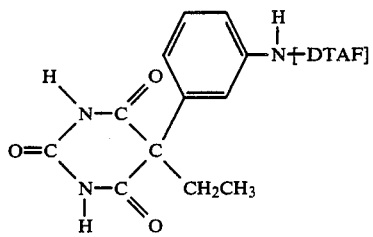

EXAMPLE XXXIV

α-aminoacetyliminostilbene-DTAF conjugate

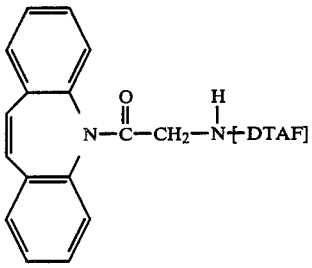

EXAMPLE XXXV

1-N-isopropylamino-2-α-aminoacetyl-3-(1'-naphthoxy)-propane-[DTAF] conjugate

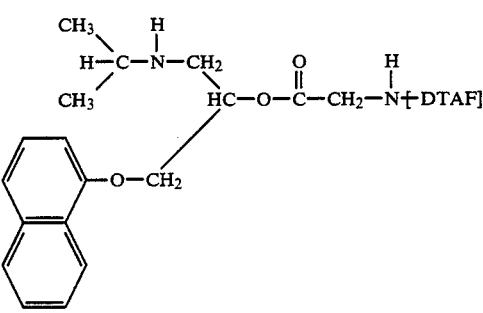

EXAMPLE XXXVI

3-dehydroxy-3-aminodigoxigenin-DTAF conjugate

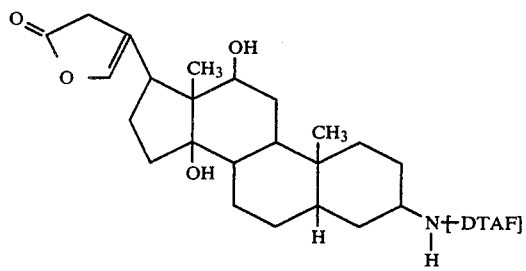

As mentioned above, the fluorescently labeled tracers prepared according to this invention can be used in a variety of immunoassay procedures in particular in a fluorescence polarization immunoassay. The following examples demonstrate the suitability of tracers of the present invention in assays employing fluorescence polarization techniques.

All examples followed the same general procedure:

(1) A small volume of standard or test serum is delivered into a test tube and diluted with buffer;

(2) A small volume of concentrated fluorescent tracer optionally containing a surfactant is then added to each tube;

(3) Finally, a volume of diluted antisera is added; and (4) The reaction mixture is incubated at room temperature.

VALPROIC ACID ASSAY
2-ETHYL-5-AMINO-PENTANOIC ACID DTAF CONJUGATE

Materials Required:

(1) Buffer: 0.1M phosphate, pH 7.5, containing 0.01% (w/v) sodium azide and 0.01% (w/v) bovine gamma globulin (BGG).

(2) Tracer: 2-ethyl-5-amino-pentanoic acid-DTAF conjugate $50 \times 10^{-9}$M in 0.1M tris hydrochloride buffer, pH 7.8, containing 0.1% (w/v) sodium dodecyl sulfate, 0.01% (w/v) bovine gamma globulin, and 0.01% (w/v) sodium azide.

(3) Antibody: Sheep antiserum to valproic acid diluted to 1 to 3.75 in buffer.

(4) Standards of unknowns: human serum (or other biological fluid) containing valproic acid in the concentration range 0 to 150 µg/ml.

(5) Fluorescence polarimeter: Instrument capable of reading the polarization of fluorescence of a $1 \times 10^{-9}$M fluorescein solution to ±0.001 polarization unit.

Protocol:

(1) 0.75 µl of standard or unknown sample placed in a 12×75 mm disposable culture tube (cuvette). This is accomplished by pipetting 20 µl of standard or unknown into a predilution container followed by 500 µl of buffer. Next 20 µl of diluted sample is pipetted into the 12×75 culture tube followed by 400 µl of buffer.

(2) 40 µl of tracer and 800 µl of buffer are added to the cuvette.

(3) 40 µl of antiserum and 800 µl of buffer are added to the cuvette. The contents of the cuvette are mixed and incubated for approximately 15 minutes at room temperature.

(4) The fluorescence polarization is read. Typical results are presented in Table I.

TABLE I

| Valproic Acid Conc. (µg/ml) | Polarization |
|---|---|
| 0 | 0.217 |
| 12.5 | 0.186 |
| 25 | 0.165 |
| 50 | 0.132 |
| 100 | 0.099 |
| 150 | 0.081 |

The polarization changes in a regular manner as the concentration of valproic acid is varied allowing the construction of a standard curve. Unknown samples are treated in an identical manner; from the polarization of fluorescence of the unknown sample, the concentration of valproic acid in the unknown sample may be determined by reference to the standard curve.

GENTAMICIN ASSAY

Materials Required:

(1) Buffer: (See valproic acid assay).

(2) Tracer: Gentamicin-DTAF at 100 nM in a trishydrochloride buffer pH 7.5 containing 0.125% sodium dodecyl sulfate, 0.01% sodium azide, and 0.01% bovine gamma globulin.

(3) Antibody: Rabbit or sheep antisera to gentamicin diluted appropriately in buffer.

(4) Standards or unknowns: human serum (or other biological fluid) containing gentamicin.

(5) Fluorescence polarimeter: (See valproic acid assay).

Protocol:

(1) 1.8 µl of standard or unknown sample is placed in a 12×75 mm disposable culture tube (cuvette). This is done by pipetting 20 µl of sample followed by 200 µl of buffer. Next 20 µl of diluted sample is pipetted into the cuvette followed by 200 µl of buffer.

(2) 40 µl of tracer and 1000 µl of buffer are added to the cuvette.

(3) 40 µl of antibody and 1000 µl of buffer are added, the contents of the cuvette are mixed and incubated for approximately fifteen minutes at room temperature.

(4) The fluorescence polarization is read following the incubation. Typical results are presented in Table II.

TABLE II

| Gentamicin Concentration (µg/ml) | Polarization |
|---|---|
| 0 | 0.178 |
| 0.5 | 0.158 |
| 1.0 | 0.140 |
| 2.0 | 0.115 |
| 4.0 | 0.090 |
| 8.0 | 0.074 |

The polarization changes in a regular manner allowing construction of a standard curve. Unknown samples are tested in an identical manner, and the gentamicin content is determined by reference to the standard curve. The utility of the gentamicin-DTAF tracer for determining the concentration of gentamicin in biological samples is thereby illustrated.

N-ACETYL PROCAINAMIDE ASSAY

Materials required:

(1) Buffer: (See valproic acid assay)

(2) Tracer: Desethyl-N-acetyl procainamide-DTAF conjugate at a concentration of $50 \times 10^{-9}$ in a 5.75% (w/v) solution of sodium toluene sulfonate.

(3) Antiserum: Rabbit antiserum to N-acetyl-procainamide diluted one to six in buffer.

(4) Standards or unknowns: human serum (or other biological fluid).

(5) Fluorescence polarimeter: (See valproic acid assay).

Protocol:

(1) 0.48 μl of standard or unknown is placed in a cuvette by pipetting 10 μl of sample into a predilution container and mixing with 200 μl of buffer. Ten μl of diluted sample is next pipetted into the cuvette followed by 200 μl of buffer.

(2) 40 μl of tracer and 1000 μl of buffer are added to the cuvette.

(3) 40 μl of antiserum and 1000 μl of buffer are next added to the cuvette. The contents of the cuvette are mixed and incubated at room temperature for approximately fifteen minutes at room temperature.

(4) The fluorescence polarization is read following the fifteen minute incubation period. Typical results for the N-acetyl-procainamide are presented in Table III.

TABLE III

| N—Acetyl Procainamide (μg/ml) | Polarization |
| --- | --- |
| 0 | 0.239 |
| 1 | 0.218 |
| 2 | 0.209 |
| 4 | 0.190 |
| 8 | 0.173 |
| 16 | 0.158 |

The standard curve can be constructed from the data in Table III. Unknown samples treated identically to the standards can be quantitated by references to the standard curve, thereby illustrating the usefullness of the standard N-acetyl procainamide-DTAF conjugate for the determination of N-acetyl-procainamide in biological fluids.

The following table summarizes the various fluorescence polarization assays that have been carried out in accordance with the above-described procedures employing tracers prepared in the preceding examples. The tracers employed are identified by Example number and the specific ligand(s) determined are indicated.

| Tracer Prepared In Example Number | Ligand(s) Assayed |
| --- | --- |
| I | Gentamicin |
| II | Tobramycin |
| III | Amikacin |
| IV | Streptomycin |
| V | Neomycin |
| VI | Vancomycin |
| VII | N—acetylprocainamide |
| VIII | N—acetylprocainamide |
| IX | N—acetylprocainamide |
| X | Primidone |
| XI | Valproic acid |
| XII | Valproic acid |
| XIII | Thyroxine (T4) |
| XIV | Thyroxine (T4) |
| XV | Thyroxine (T3) |
| XVI | Nortrptyline; Amitriptyline |
| XVII | Nortrptyline; Amitriptyline |
| XVIII | Nortrptyline; Amitriptyline |
| XIX | Imipramine; Desipramine |
| XX | Imipramine; Desipramine |
| XXI | Theophylline |
| XXII | Theophylline |
| XXIII | Quinidine |
| XXIV | Valproic acid |
| XXV | Disopyramide |
| XXVI | Disopyramide |
| XXVII | Salicylate |
| XXVIII | Procainamide |
| XXIX | Chloroamphenicol |
| XXX | Phenytoin |
| XXXI | Salicylate |
| XXXII | Propranolol |
| XXXIII | Phenobarbital |
| XXXIV | Carbamazepine |
| XXXV | Propranolol |
| XXXVI | Digoxin |

As evident from the above results, the tracers of the present invention are effective reagents in fluorescence polarization immunoassays. In addition to the properties mentioned above, the tracers of the present invention posses a high degree of thermal stability, a high degree of bound polarization, high quantum yields and are relatively easy to produce and purify.

Although this invention has been described with respect to specific modifications, the details thereof are not to be construed as limitations, for it will be apparent that various equivalents, changes and modifications may be restorted to without departing from the spirit and scope thereof and it is understood that such equivalent embodiments are intended to be included therein.

What is claimed is:

1. A compound useful in a fluorescence polarization immunoassay for determining aminoglycosides, which compound has the formula:

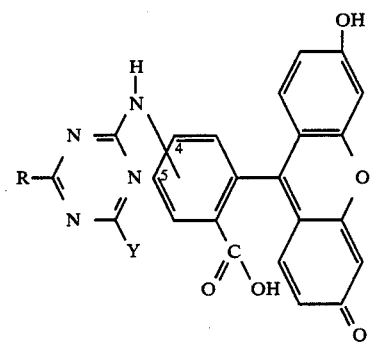

wherein
Y is halo or lower alkyl; and
R is a ligand-analog having a molecular weight within the range of 50 to 4000 wherein said ligand-analog has at least one common epitope with an aminoglycoside ligand so as to be specifically recognizable by a common antibody;
and biologically acceptable salts thereof.

2. A compound of claim 1 wherein Y is halo.

3. A compound of claim 2 wherein Y is chloro.

4. A compound according to claim 1 wherein R is gentamicin.

5. A compound according to claim 1 wherein R is tobramycin.

6. A compound according to claim 1 wherein R is amikacin.

7. A compound according to claim 1 wherein R is streptomycin.

* * * * *